US 6,718,742 B1
Apr. 13, 2004

(12) United States Patent
Baker

(54) MAGNETIC PARTICLE COMPOSITION

(75) Inventor: Matthew John Baker, Maidstone (GB)

(73) Assignee: DNA Research Innovations Limited, Kent (GB)

( * ) Notice: Subject to any disclaimer, the term of this patent is extended or adjusted under 35 U.S.C. 154(b) by 0 days.

(21) Appl. No.: 10/111,064

(22) PCT Filed: Jun. 30, 2000

(86) PCT No.: PCT/GB00/02545

§ 371 (c)(1),
(2), (4) Date: Sep. 27, 2002

(87) PCT Pub. No.: WO01/03149

PCT Pub. Date: Jan. 11, 2001

(30) Foreign Application Priority Data

Jul. 2, 1999 (GB) .............................................. 9915398

(51) Int. Cl.$^7$ .................................................... C08J 5/20
(52) U.S. Cl. ........................................... 54/28; 524/431
(58) Field of Search ............................. 521/28; 524/431

(56) References Cited

U.S. PATENT DOCUMENTS

| 5,091,206 A | * | 2/1992 | Wang et al. | ................ 427/2.18 |
| 5,714,536 A | * | 2/1998 | Ziolo et al. | .................. 524/430 |
| 5,792,445 A | * | 8/1998 | Tournier et al. | .......... 424/9.322 |

FOREIGN PATENT DOCUMENTS

DE          196 24 426        *  1/1998

* cited by examiner

*Primary Examiner*—Bernard Lipman
(74) *Attorney, Agent, or Firm*—Dann, Dorfman, Herrell & Skillman, P.C.

(57) ABSTRACT

A magnetic particle composition which can be used for separating biomolecules comprises magnetic materials of preferably less than five micron diameter bound to a negatively charged ion exchanger. The composition can be used to separate DNA from mixtures and to separate out cell debris.

29 Claims, No Drawings

MAGNETIC PARTICLE COMPOSITION

The present invention relates to a method of making magnetic and paramagnetic particles which can be used in the separation of biomolecules or compounds from laboratory to industrial scale volumes.

In order to separate biomolecules such as nucleic acids from mixtures containing them it is known to use magnetic particles which are coated with a coating which will attach to the biomolecule which is to be separated. The particles are then added to the mixture and the particles attached to the biomolecules can be separated by use of a magnetic field.

The magnetic particles or beads must be of a size which enables them to remain in suspension in the liquids used. However if they are too small or contain fines or other similar particles they can stay in suspension and can be too slow to separate.

Known methods of making magnetic and paramagnetic particles include

1) Incorporation of magnetite (iron oxide, $Fe_3O_4$) inside porous agarose or cellulose followed by grinding or sieving to obtain a range of particle diameters, usually 1 to 10 microns.
2) Incorporation of magnetite inside silica followed by grinding or sieving to obtain a range of particle diameters, usually 1 to 10 microns.
3) Production of magnetite (less than 10 microns) by precipitation of iron salts, followed by surface coating with a silane or other functional group.
4) Coating a mono-disperse polystyrene bead (less than 10 microns) with submicron iron oxide, followed by another coating of polystyrene with or without functional groups.
5) Internal precipitation of iron oxide into a mono disperse polystyrene bead (less than 10 microns) followed by surface coating with functional groups.

Typically, magnetic beads have a diameter of less than 10 microns otherwise their sedimentation rates are too high under gravity for easy handling and the surface area too low to bind desired amount of the target molecule. Some larger beads such as agarose-magnetite may be up to 100 microns but they rely on being very porous to bind target molecules internally and separate out under gravity extremely quickly.

U.S. Pat. Nos. 4,695,392 and 5,091,206, WO 96/18731, EP 515484B1 disclose methods of forming and using such magnetic particles.

I have devised improved magnetic particles and a method of making them.

According to the invention there is provided a magnetic particle composition which comprises a magnetic material combined with negatively charged ion exchanger.

The invention also provides a method of forming a magnetic particle composition which method comprises contacting a magnetic material with a negatively charged ion exchanger.

The magnetic materials preferably have a diameter of less than ten microns and more preferably five microns or less.

The magnetic material can be any of the conventionally used magnetic materials such as magnetite, iron oxides, transition metal oxides or any ferro or paramagnetic material.

The ion exchanger can be porous or non porous and ion exchangers which can be used include polymethacrylate carboxy ion-exchangers, silica particles coated with a negative charge, cellulose or agarose with phosphate or sulphate groups or any negatively charged species.

The ion exchanger can be attached directly to the magnetic material e.g. by charge alone or it can be attached using a binding agent such as polymerised acrylic acid, or any agent that forms a coating or surface coat to aid cohesion of the materials. The particle may be further derivatised with functional groups such as carboxy, amine, imidazole etc.

The composition can readily be formed by mixing the components in powder form or by pre-mixing in aqueous or non-aqueous solutions with or without the binding agent.

The compositions of the invention i.e. the magnetic material combined with the ion exchanger, preferably have a diameter of between 0.5 microns to 1 mm and more preferably of 20 to 150 microns in diameter.

The ratio of magnetic particle to ion exchanger is not critical and can be varied in accordance with the application, typical ratios are from 5 to 50% (w/w) iron oxide.

Preferably a suspension of the particle composition of the invention in a liquid containing the material to be separated can be easily handled in conventional fluid handling and dispensing systems.

It is a feature of the present invention that the particle compositions provide faster magnetic separation or sedimentation under gravity in larger volumes without residual fines or particles remaining in suspension. The larger particles e.g 20 to 150 microns, also remain in suspension four longer compared to other magnetic beads of similar size made from other materials thus retaining effective mixing and binding kinetics.

The particles can be kept in suspension for dispensing with minimal agitation and also are preferably able to pass through standard pipette tips.

The compositions of the present invention can be used to separate biomolecules from mixtures containing them, for example they can be used to separate nucleic acids and to purify solutions or suspensions by removing impurities such as cell debris etc.

When the compositions are to be used to separate a biomolecule from a liquid containing the biomolecule the particle composition is contacted with a binding agent for the biomolecule for example biotinylated biomolecules may be isolated using Streptavidin coated magnetic particles.

The invention also provides a method for separating biomolecules from mixtures containing them which method comprises contacting a liquid suspension of the biomolecule with the magnetic particle composition as described above to form a suspension of the magnetic particle composition in which the particle composition binds to the biomolecule and applying a magnetic field to the suspension to separate out the magnetic particles having the biomolecule bound thereto.

The biomolecule can be separated from the magnetic particles by conventional means.

The method of the invention can be used to remove cellular debris or insoluble material without centrifugation or filtration.

For example, in the removal of cellular debris from a microbial, plasmid or plant DNA extraction, the particles can be used to rapidly remove unwanted contaminants leaving the target DNA in solution.

The invention is further described in the following examples.

EXAMPLE 1

6 grams of a granular, porous polymethacrylate carboxy ion-exchanger (100–500 mesh) was mixed with 2 grams of magnetite ($Fe_3O_4$) of 5 microns diameter or less. This material was then washed in 2% Tween 20 with 1M sodium chloride and used to extract DNA from blood for example: 100 mg of the magnetic beads described above were mixed with 1 ml of whole blood pre-diluted in 10 mM Ammonium Bicarbonate, 1% Tween 20, pH 9. The bound DNA was washed free of contaminants with water and eluted using 10 mM Tris pH 9 at 80° C.

EXAMPLE 2

6 grams of a granular, porous polymethacrylate carboxy ion-exchanger, (100–500 mesh) was mixed with 2 grams of magnetite ($Fe_3O_4$) of less than 5 microns diameter This material was then mixed with 50 ml of 2% v/v acrylic acid, 2% Ammonium persulphate and heated to 70° C. for 30 minutes. This material was then washed in detergents and salts and used to extract DNA from blood as described above.

EXAMPLE 3

6 grams of a granular, porous polymethacrylate carboxy ion-exchanger (100–500 mesh) was mixed with 2 grams of magnetite ($Fe_3O_4$ less than 5 microns). This material was then mixed with 50 ml of 2% v/v acrylic acid, 2% Ammonium persulphate plus 0.02% divinyl benzene and heated to 70° C. for 30 minutes.

EXAMPLE 4

An overnight culture of *E.coli* was prepared containing a high copy number plasmid. 1 ml of this culture was adjusted to 0.1 M NaOH with 1% SDS and mixed gently for 5 minutes. Then the magnetic particles as described in Example 1 were added and the suspension adjusted to 1 M potassium acetate pH 5.5. Following magnetic separation all the insoluble debris was removed in less than 1 minute leaving a clarified supernatant containing plasmid DNA ready for further processing.

What is claimed is:

1. A magnetic particle composition which consists essentially of a magnetic material combined with a negatively charged ion exchanger, wherein the particles have a diameter between 20 microns and 1 mm and wherein the composition is formed by mixing a powder of a magnetic material with a powder of a negatively charged ion exchanger.

2. The magnetic particle composition of claim 1, wherein the particles have a diameter between 20 and 150 microns.

3. The magnetic particle composition of claim 1, wherein the composition is formed by mixing a powder of a magnetic material with a powder of a negatively charged ion exchanger.

4. The magnetic particle composition of claim 3, wherein the mixing takes place in the presence of a binding agent.

5. The magnetic particle composition of claim 1, wherein the magnetic material is a particle having a diameter of less than 10 microns.

6. The magnetic particle composition of claim 5, wherein the magnetic material is a particle having a diameter of less than 5 microns.

7. The magnetic particle composition of claim 6, wherein the magnetic material is a particle having a diameter of less than 1 micron.

8. The magnetic particle composition of claim 1, wherein the ion exchanger is non porous.

9. The magnetic particle composition of claim 1, wherein the ion exchanger is a polymethacrylate carboxy ion-exchanger.

10. The magnetic particle composition of claim 1, wherein the ion exchanger is attached directly to the magnetic material.

11. The magnetic particle composition of claim 1, wherein the particles are formed in the presence of a binding agent.

12. The magnetic particle composition of claim 11, wherein the binder is selected from the group consisting of an acrylic acid monomer, an acrylic acid polymer, acrolein, an amine, an amide, an alcohol, an aldehyde, an organic acid, an imidazole, a phosphate, a secondary amine, a secondary sulphate, a tertiary amine, a tertiary sulphate, a quaternary amine and a quaternary sulphate.

13. The magnetic particle composition of claim 1, wherein the ratio of magnetic material to ion exchanger is from 0.05 to 0.2.

14. A method of forming a magnetic particle composition consisting essentially of a magnetic material combined with a negatively charred ion exchanger, wherein the particles have a diameter between 20 microns and 1 mm, the method comprising mixing a powder of a magnetic material with a powder of a negatively charged ion exchanger.

15. The method of claim 14, wherein the particles have a diameter between 20 and 150 microns.

16. The method of claim 14, wherein the mixing takes place in the presence of a binding agent.

17. The method of claim 14, wherein the magnetic material is a particle having a diameter of less than 10 microns.

18. The method of claim 17, wherein the magnetic material is a particle having a diameter of less than 5 microns.

19. The method of claim 18, wherein the magnetic material is a particle having a diameter of less than 1 micron.

20. The method of claim 14, wherein the ion exchanger is non porous.

21. The method of claim 14, wherein the ion exchanger is a polymethacrylate carboxy ion-exchanger.

22. The method of claim 14, wherein the ion exchanger is attached directly to the magnetic material.

23. The method of claim 16, wherein the binder is selected from the group consisting of an acrylic acid monomer, an acrylic acid polymer, acrolein, an amine, an amide, an alcohol, an aldehyde, an organic acid, an imidazole, a phosphate, a secondary amine, a secondary sulphate, a tertiary amine, a tertiary sulphate, a quaternary amine and a quaternary sulphate.

24. The method of claim 14, wherein the ratio of magnetic material to ion exchanger is from 0.05 to 0.2.

25. A magnetic particle made by the method of claim 14.

26. A method of separating biomolecules from mixtures containing them, the method comprising:

contacting a liquid suspension of the biomolecules with a magnetic particle composition;

forming a suspension of said magnetic particle composition and said suspension of biomolecules in which the magnetic particle composition binds to the biomolecules; and applying a magnetic field to the suspension to separate out the magnetic particles having the biomolecules bind thereto;

wherein said magnetic particle composition consisting essentially of a magnetic material combined with a negatively charged ion exchanger and wherein the particles have a diameter between 20 microns and 1 mm and wherein the composition is formed by mixing a powder of a magnetic material with a powder of a negatively charged ion exchanger.

27. The method of claim 26, wherein the magnetic particles bind nucleic acid present in a mixture with impurities.

28. The method of claim 27, wherein the nucleic acid is selected from the group consisting of microbial DNA, plant DNA and plasmid DNA.

29. The method of claim 27, wherein the impurities are cellular debris or insoluble material.

* * * * *